United States Patent [19]

DePrince et al.

[11] Patent Number: 4,898,733
[45] Date of Patent: Feb. 6, 1990

[54] LAYERED, COMPRESSION MOLDED DEVICE FOR THE SUSTAINED RELEASE OF A BENEFICIAL AGENT

[75] Inventors: Randolph B. DePrince; Ravi Viswanathan, both of Terre Haute, Ind.

[73] Assignee: International Minerals & Chemical Corp., Terre Haute, Ind.

[21] Appl. No.: 794,530

[22] Filed: Nov. 4, 1985

[51] Int. Cl.$^4$ ................................................ A61F 2/00
[52] U.S. Cl. ..................................... 424/425; 424/426; 424/473; 424/474; 424/490
[58] Field of Search ............... 424/468, 472, 474, 475, 424/480, 424, 461, 472, 473, 484, 425, 426, 489, 486

[56] References Cited

U.S. PATENT DOCUMENTS

| | | | |
|---|---|---|---|
| 2,951,792 | 9/1960 | Swintosky | 424/472 |
| 3,279,996 | 10/1966 | Long, Jr. et al. | 424/424 |
| 3,317,394 | 5/1967 | Fryklof et al. | 424/472 |
| 3,362,880 | 1/1968 | Jefferies | 424/472 X |
| 3,832,252 | 8/1974 | Higuchi et al. | 424/424 X |
| 3,923,939 | 12/1975 | Baker et al. | 264/49 |
| 3,965,255 | 6/1976 | Bloch et al. | 424/472 X |
| 4,220,152 | 9/1980 | Dresback | 424/473 X |
| 4,289,795 | 9/1981 | Bogentoft et al. | 427/3 |
| 4,298,003 | 11/1981 | Theeuwes et al. | 424/424 |
| 4,326,525 | 4/1982 | Swanson et al. | 128/260 |
| 4,341,759 | 7/1982 | Bogentoft et al. | 424/21 |
| 4,352,883 | 10/1982 | Lim | 424/424 |
| 4,576,604 | 3/1986 | Guittard et al. | 604/890 |
| 4,578,264 | 3/1986 | Stricker et al. | 424/461 X |
| 4,609,374 | 9/1986 | Ayer | 424/473 X |
| 4,610,870 | 9/1986 | Jain et al. | 424/19 |
| 4,629,620 | 12/1986 | Lindahl et al. | 424/473 |
| 4,666,702 | 5/1987 | Junginger | 424/473 |
| 4,681,755 | 7/1987 | Colombo et al. | 424/486 |

FOREIGN PATENT DOCUMENTS

| | | | |
|---|---|---|---|
| 0942667 | 2/1974 | Canada | 424/425 |
| 2058565 | 4/1981 | United Kingdom | 424/472 |
| 2123289 | 2/1984 | United Kingdom | 424/472 |

*Primary Examiner*—Thurman K. Page
*Attorney, Agent, or Firm*—Wendell Ray Guffey; Thomas L. Farquer

[57] ABSTRACT

A device for the continuous administration of a beneficial agent to a living being at a substantially steady rate which comprises:
(a) a body fluid-contacting layer which comprises a dispersion of an agent which is substantially soluble in the body fluid and a solid matrix material, said matrix material comprising a polymer which is substantially insoluble in said body fluid, and
(b) a non-body fluid-contacting layer which comprises said beneficial agent, wherein said body fluid-contacting layer is compression molded to said non-body fluid contacting layer.

24 Claims, 3 Drawing Sheets

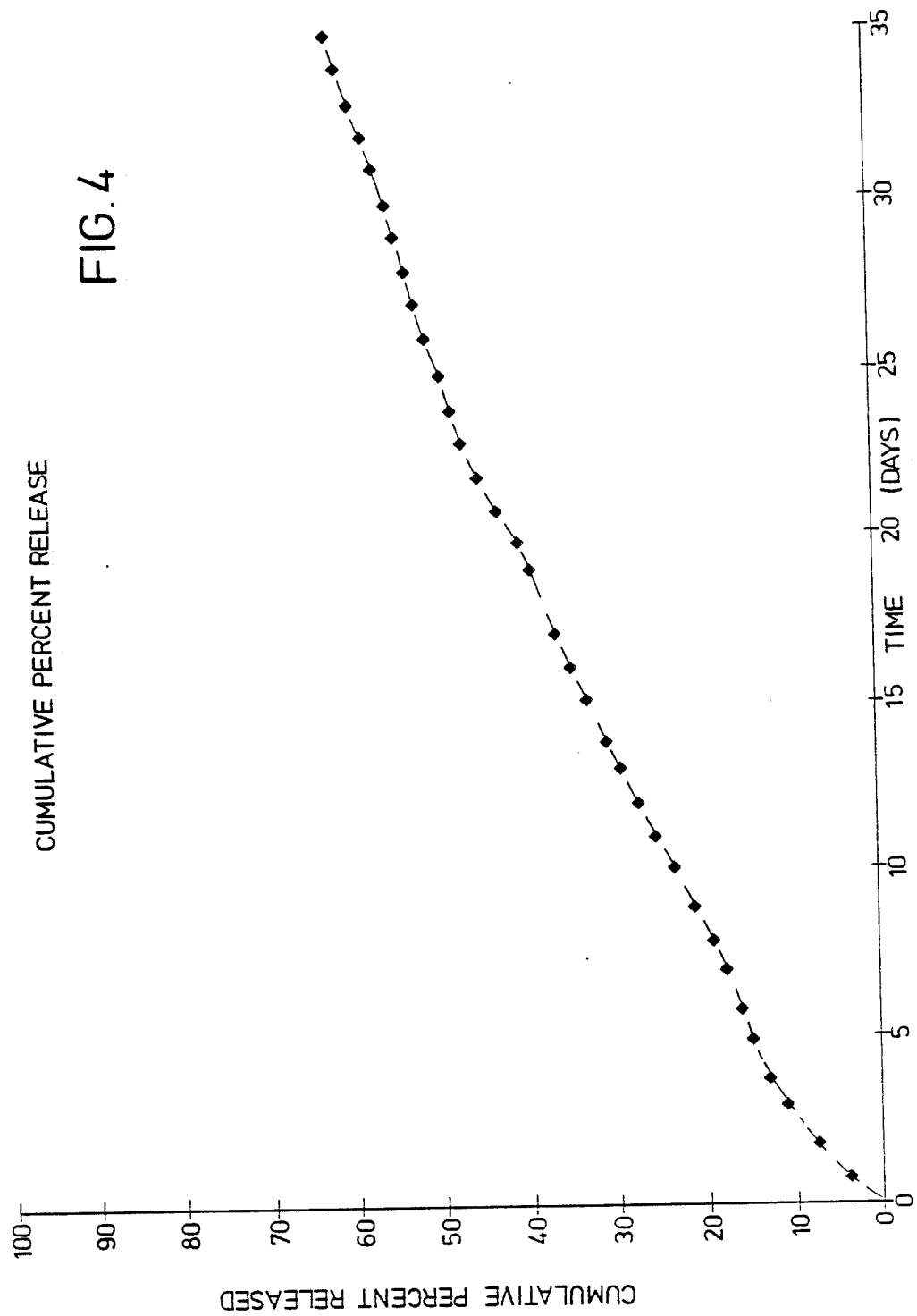

4,898,733

LAYERED, COMPRESSION MOLDED DEVICE FOR THE SUSTAINED RELEASE OF A BENEFICIAL AGENT

FIELD OF THE INVENTION

This invention relates to a device for the continuous administration of a beneficial agent in the body of a living being. More specifically, this invention relates to such a device which comprises at least two layers which have been compression molded.

BACKGROUND OF THE INVENTION

Beneficial agents of various kinds can be administered to a living being in a variety of ways. Frequently, they are administered in some type of tablet or capsule. These are popular means of administration, for they are both convenient and easy to use. In their most simple form, tablets and capsules comprise a homogenous mixture of the beneficial agent and a carrier of some sort. Typically, the beneficial agent is released fairly rapidly from these forms, leading to an initial high concentration of the beneficial agent in the body which rapidly decreases.

Frequently, it would be advantageous to deliver a beneficial agent to a living being over a prolonged period of time and, preferably, at a substantially steady rate. A variety of devices are known for the sustained release of beneficial agents. In some such devices, the agent is dispersed in a polymer matrix which may be permeable to the agent by diffusion or which may be microporous, the pores containing an agent-permeable medium such that the agent will preferentially dissolve in and permeate through that medium.

Other devices are characterized by a reservoir which holds the agent and, perhaps, a carrier, and which is surrounded by a wall or barrier of some sort. The wall may be a semipermeable material that allows body fluid into the reservoir but does not allow the beneficial agent to exit. In such a device there may be a passageway in the wall which allows the solution of agent-containing body fluid to pass from the device into the tissues of the body. Alternatively, the wall may be impermeable in part and permeable in part, such that the beneficial agent can diffuse through the permeable portion over time.

As indicated above, a wide variety of devices have been suggested or designed in recent years. A frequent shortcoming of these devices, however, has been either that they could not be used to obtain a substantially steady rate of release of the beneficial agent over time (otherwise described as a rate of release approaching zero order) or, if they did provide a substantially steady release rate, they were difficult and time-consuming to construct. For example, U.S. Pat. No. 4,289,795, issued to Bogentoft et al., discloses a method for preparing a delivery system having controlled release of an active component wherein a particle is coated in a continuous coating operation with a composition which comprises the active component and an inactive release-controlling substance. The concentration of the active component is decreased as the coating operation progresses. Such a method, which calls for repeated coating steps and changes in the composition of the coating material during the coating process, is impractical for large-scale, commercial use.

Accordingly, it is an object of this invention to provide a device for the sustained release of a beneficial agent that is relatively easy to make and provides for a substantially steady rate of release of the agent.

It is a further object of this invention to provide such a device that can be used with a wide variety of beneficial agents.

It also is an object of the present invention to provide such a delivery device in a variety of sizes and shapes and in a form suitable for oral ingestion, implantation into the tissues of a body or insertion into a body cavity.

Additional objects of the present invention shall become apparent to those skilled in the art from the description of the invention below taken in conjunction with the accompanying claims and figures.

SUMMARY OF THE INVENTION

In accordance with the present invention, there is disclosed a device for the continuous administration of a beneficial agent to a living being at a substantially steady rate which comprises (a) a body fluid-contacting layer which comprises a dispersion of an agent which is substantially soluble in body fluid and a solid matrix material, said matrix material comprising a polymer which is substantially insoluble in said body fluid, and (b) a non-body fluid-contacting layer which comprises said beneficial agent, wherein said body fluid-contacting layer is compression molded to said non-body fluid-contacting layer.

The present invention also is directed to a method of administering a beneficial agent by implanting the device in the tissues of a living being, inserting it into a body cavity of a living being, or through oral ingestion of the device.

BRIEF DESCRIPTION OF THE DRAWINGS

FIG. 4 is a graph illustrating the cumulative percent released from these devices during the time of the trial.

DETAILED DESCRIPTION OF THE INVENTION

Figure 1:
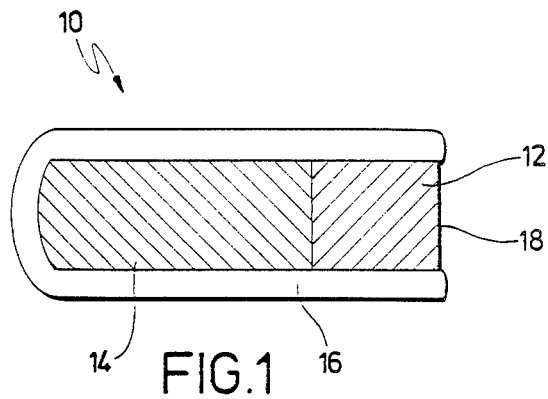
FIG. 1 depicts a cross-section of a device of this invention showing a non-body fluid-contacting layer and a body fluid-contacting layer, partially overlaid with an impermeable coating.

This invention relates to novel devices for the continuous administration of a beneficial agent in the body of a living being over a prolonged period of time and at a substantially steady rate of release. The device comprises a compression molded tablet or pellet which comprises at least two layers. The tablet comprises at least one layer which, when the device is implanted into body tissues, inserted into a body cavity or orally ingested, will come into direct contact with body fluids. It also comprises one layer which will not come into direct contact with body fluids.

The body fluid-contacting layer (or layers) of this device comprises a dispersion of an agent which is substantially soluble in body fluids in a solid matrix material through which the agent can be released by diffusion.

The matrix material comprises a polymer which is substantially insoluble in body fluids. This layer is compression molded to a non-body fluid-contacting layer which is in the form of a reservoir and comprises the beneficial agent to be administered to the living being. When the device is placed within the body of a living being (by means of implantation, insertion or oral ingestion), the matrix layer will come into contact with body fluids, and the body fluid-soluble agent will begin to dissolve in the body fluids and leach out of the matrix, leaving pores or channels in the matrix. Once sufficient body fluid-soluble agent has diffused out of the matrix that the channels extend through the body fluid-contacting layer to the non-body fluid-contacting layer, beneficial agent will begin to diffuse from the non-body fluid-contacting layer through the channels and out of the device.

Typically, the body fluid-contacting layer will comprise about 30 to 70 parts soluble agent to about 70 to about 30 parts polymer. The preferred range is about 40 to about 60 parts agent to about 60 to about 40 parts polymer. The ratio of agent to polymer can be extended beyond these general guidelines depending upon such factors as the type of beneficial agent and polymer and the desired thickness of the layer. For example, the layer may comprise only 20 to 10 percent agent if the layer is relatively thin, provided that body fluid which comes into contact with the layer can migrate all the way through the layer and provide channels through which the beneficial agent in the non-body fluid-contacting layer can pass to be released from the device. The relative amounts of agent and polymer desirable in the body-fluid contacting layer of a specific device can be determined by one skilled in the art using conventional methodology.

The non-body fluid-contacting layer acts as a reservoir which comprises the beneficial agent of interest. The reservoir also may comprise a small amount of the polymer used in the body fluid-contacting layer, or another material, which can act as a binder when the two layers are compression molded together. Such a material can be included in the reservoir if the beneficial agent itself is unable to bind to the other layer to form the tablet. Typically, if a binder is added to the agent, the binder does not exceed about 10 to about 20 percent by weight of the total weight of agent and binder.

The components for the non-body fluid-contacting layer and body fluid-contacting layer are compression molded together, using conventional techniques, to form a tablet or pellet. This tablet then may be partially coated or covered with a material which is substantially impermeable to body fluid and to the beneficial agent, leaving all or a portion of the body fluid-contacting layer uncoated. It is through this non-coated region that body fluid and beneficial agent will diffuse once the tablet has been placed within the body of a living being.

Applicants have discovered that by constructing a layered, compression molded delivery device as described herein the delivery of beneficial agent from the device to surrounding body tissue can be more easily controlled than with conventional devices, such that a release order approaching zero can be obtained and maintained for an extended period of time. The device is constructed such that there is a distinct difference between the concentration of the body fluid-soluble agent in the outer, body fluid-contacting layer and the concentration of the beneficial agent in the inner, non-body fluid-contacting layer such that the former layer acts as a matrix system and the latter can be characterized as a reservoir system. The body fluid-contacting matrix layer with its channels, through which the beneficial agent passes as it exits the reservoir, acts as a diffusion barrier and controls the entrance of body fluid into the device and the diffusion of beneficial agent and body fluid out of the device and into the body of the living being. The diffusion rate of beneficial agent from any device of this invention is determined by a number of parameters, including the surface area of the body fluid-contacting layer which is exposed to the body fluid, its thickness, and its porosity, which is determined by its concentration of body fluid-soluble agent. Other factors include the relative sizes of the body fluid-contacting and non-contacting layers, the number of body fluid-contacting layers, and the solubility of the beneficial agent in the body fluid.

In one embodiment of this invention, the device disclosed and claimed herein comprises more than one body fluid-contacting layer. For example, the device may comprise two body fluid-contacting layers which are compression molded to opposite ends of a non-body fluid-contacting layer which comprises a reservoir of beneficial agent. This type of device may be beneficial, for example, when practical constraints on size of the device and on the diameter of the releasing surface area limit the rate of release below that desired. In such a situation, the rate of release can be increased by providing two body fluid-contacting layers and, therefore, two releasing surfaces.

In the specification and claims, the term "beneficial agent" is defined as an agent that produces a physiologically or pharmacologically useful effect in the body of a living being either at a site in close proximity to its point of release or at a site removed from the release site. The term includes, but is not limited to, drugs, vitamins, nutritional supplements, and biologically active proteins. The term "drug" includes hypnotics and sedatives, tranquilizers, anti-convulsants, muscle relaxants, analgesics, anti-inflammatory agents, local anesthetics, antimicrobials, androgenic, progestational and estrogenic steroids, sympathomimetic drugs and diuretics. The beneficial agent may be present as a pharmacologically acceptable derivative that can pass through the body in a body fluid and can be converted to the active agent within the body through the action of body enzymes-assisted transformation, pH, activity by a specific organ, or other similar action. The amount of beneficial agent in the device, taken as a whole, is limited basically only by considerations regarding the size of the device and is an amount at least equal to an amount that, upon release from the device, will bring about the agent's desired pharmaceutical or pharmacological effect.

The matrix material of the body fluid-contacting layer may be selected from any of a wide group of polymers that are substantially insoluble in, but biologically compatible with, aqueous based body fluids such as tear fluids, tissue juices, water and the like. Such polymers include acyl substituted cellulose acetates and alkyl derivatives thereof, partially and completely hydrolyzed alkylene-vinyl acetate copolymers, unplasticized polyvinyl chloride, cross-linked homo- and copolymers of polyvinyl acetate, cross-linked polyesters of acrylic and methacrylate, polyvinyl alkyl ethers, polyvinyl fluoride, silicone, polycarbonate, polyurethane, polyamide, polysulphones, styrene acrylanitrile copolymers, cross-linked poly(ethylene oxide), poly- (alkylenes), poly(vinyl imidazole), poly(esters), chlorosulphonated polyolefins and ethylenevinyl ester copolymers. The ethylene-vinyl ester copolymers may include ethylene- vinyl acetate, ethylene-vinyl methylacetate, ethylene- vinyl ethylacetate, and ethylene-vinyl propylacetate. Typically, to make the body fluid-contacting layer of a device in accordance with this invention, the chosen polymer is comminuted, then mixed with the body fluid- soluble agent.

The agent that is mixed with the polymeric material to form the body fluid-contacting layer is an agent which is essentially soluble in the body fluid and is biocompatible with body fluid, body tissues and organs. Such agents may be selected from a wide variety of compounds, including sodium chloride, water-soluble carbohydrates such as insulin, reducing sugars such as lactose, and non-reducing sugars such as sucrose. Other compounds also may be useful as the agent. For example, if the beneficial agent selected to be released from the non-body fluid-contacting layer also is readily soluble in body fluid, it may comprise the agent mixed with the polymer in the body fluid-contacting layer. In this embodiment of the invention, the concentration of beneficial agent in the non-body fluid-contacting layer exceeds the concentration of beneficial agent in the body fluid-contacting layer such that the former still acts as a reservoir system and the latter acts as a matrix system.

As noted above, a binder may be added to the non-body fluid-contacting layer. This binder may comprise the polymeric material used to form the matrix in the body fluid-contacting layer, or a similar polymer, or it may comprise compounds such as sodium bentonite, ethyl cellulose, stearic acid, calcium stearate, adipic acid, fumaric acid, polyethylene glycol, and cellulose acetate. Generally, the binder is present in amounts of from about 0.5 to about 20 percent by weight of the total weight of the non-body fluid contacting layer. Preferably, the binder is present in amounts of from 1 to about 10 percent by weight. It may be desirable to add a binder to the beneficial agent in this layer in order to enhance the latter's ability to be compression molded into a tablet with the agent-polymer matrix of the body-fluid-contacting layer.

Figure 2:
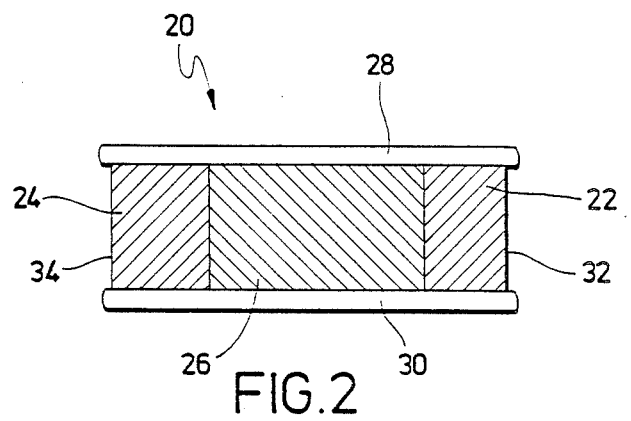
FIG. 2 depicts a cross-section of a device of this invention showing a non-body fluid-contacting layer which is sandwiched between two body fluid-contacting layers; the device partially overlaid with an impermeable coating.

The components for the body fluid-contacting- and non-contacting-layers are compression molded in accordance with conventional techniques known in the art. Once the tablet has been made it generally is further treated by placing some sort of a barrier around any exposed sides of the non-body fluid-contacting layer such that no part of the layer can come into contact with body fluid once the tablet is placed within the body of a living being. This can be accomplished by partially coating the tablet with a coating material which is substantially impermeable to body fluids and to the beneficial agent and substantially insoluble in body fluids. As illustrated in FIGS. 1 and 2, the body fluid-contacting layer also may be partially covered to more fully control the surface area of that layer through which the agents can be released. Alternatively, the tablet may be placed in a sleeve made of material substantially impermeable to body fluid and agents and substantially insoluble in body fluids. This sleeve may be open at one end (for devices having one body fluid-contacting layer) or at both ends (for devices having two body fluid contacting layers compression molded to opposite sides of the non-body fluid contacting layer). Suitable sleeve materials include acyl substituted cellulose acetates and alkyl derivatives thereof; partially and completely hydrolyzed alkylene-vinyl acetate copolymers; unplasticized polyvinyl acetate, cross-linked homo- and copolymers of polyvinyl acetate; cross-linked polyesters of acrylic and methacrylic acid, polyvinyl alkyl ethers, polyvinyl fluoride, silicone, polycarbonate, polyurethane, polyamide, polysulphones, polyimides, polyolefins, polybenzimidazoles; styrene acrylonitrile copolymers, cross-linked poly(ethylene oxide), poly(alkylenes), poly(vinyl imidazole), poly(esters), chlorosulphonated polyolefins and ethylene-vinyl ester copolymers such as ethylene-vinyl acetate. A preferred material is silicone.

The device then may be implanted in the tissues of a living being, inserted into a body cavity or orally ingested for the continuous administration of the beneficial agent.

Two embodiments of the delivery devices of this invention are shown in the figures accompanying this application. These figures represent examples of the delivery devices of this invention and, as such, are not to be construed as limiting.

FIG. 1 shows a cross-section of a device 10 which is of a size and shape for easy placement and prolonged retention in the body of a living being for the sustained, continuous release of a beneficial agent. The device comprises an outer, body fluid-contacting, layer 12 which comprises a dispersion of the beneficial agent in a polymeric matrix material. The layer 12 has been compression molded to an inner, non-body fluid-contacting, layer 14 which comprises a reservoir of beneficial agent. The two layers 12 and 14 are partially coated with an impermeable coating 16. One end 18 of the device is uncoated, providing a passageway for body fluid and beneficial agent to pass through the body fluid contacting layer of the device by diffusion.

FIG. 2 depicts a cross-section of a device 20 which also is of a size and shape for easy placement and prolonged retention in the body of a living being for the sustained and continuous release of a beneficial agent. The device comprises two body fluid-contacting layers 22 and 24, each of which comprises a dispersion of the beneficial agent to be released in a polymeric matrix material. These layers 22 and 24 have been compression molded to opposite ends of a non-body fluid contacting layer 26 which comprises a reservoir of beneficial agent. An impermeable coating, shown here as outer walls 28 and 30, is applied, leaving ends 32 and 34 uncoated.

The delivery devices of the present invention have been described above in terms of certain agents, additives, and structures. It is to be realized, however, that the materials and structures may be varied without departing from the scope and concept of this invention. The invention is further illustrated by the following examples, which are not to be construed as limiting.

EXAMPLE I

Making a Delivery Device in Accordance with the Present Invention

Ethylene vinyl acetate (EVAc) copolymer beads (40% vinyl acetate content, obtained from Aldrich Chemical Co., Milwaukee, WI) were cryogenically ground in an analytical mill with cryogenic attachment. The ground polymer then was cryogenically sieved to a particle range of 250 to 75 microns. The comminuted EVAc then was mixed with lysozyme (obtained from Sigma Chemical Co., St. Louis, MO) which had been sieved to a particle range of 250 to 75 micron in ratios of 1:1 and 1:9.

Forty mg of the 1:1 mixture were loaded into a 3/16 inch diameter mold, 120 mg of the 1:9 mixture were loaded into the mold on top of the previously loaded 40 mg. Finally another 40 mg of the 1:1 mixture were placed into the mold on top of the 1:9 mixture.

The mold was placed in a carver press and 600 psi were applied to it for 2 minutes at room temperature. After removal from the mold, the implant was inserted into a piece of silicone tubing (ID 5/32) which was open at both ends.

EXAMPLES II

Delivery of an Agent Using the Device of Example I

A set of layered devices (5 devices) were prepared as in Example I. Each device in the set consisted of 40 mg of 50% lysozyme-50% ethylene vinyl acetate (EVA) on each end and 120 mg of 90% lysozyme-10% EVA in the middle.

Figure 3:
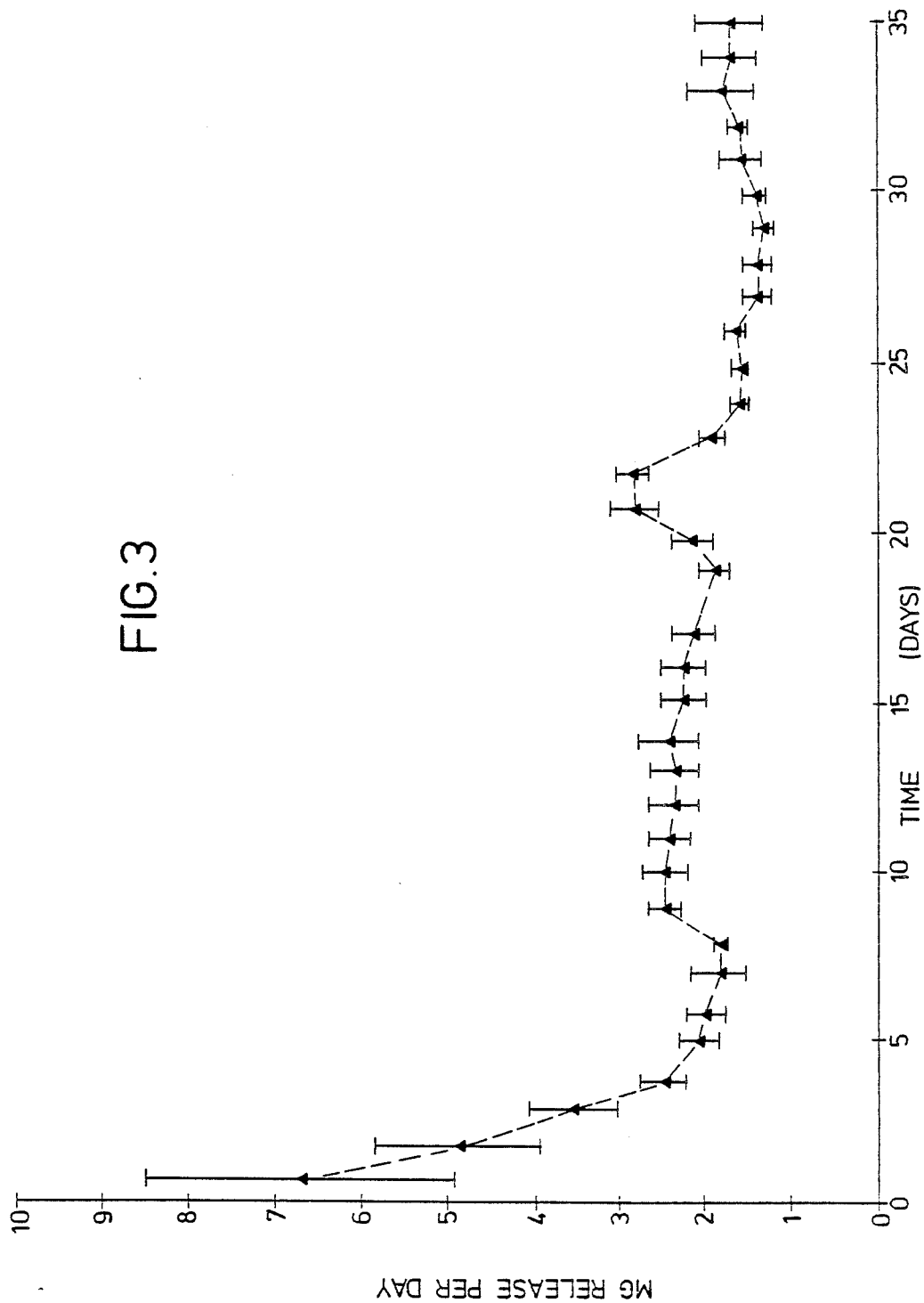
FIG. 3 is a graph illustrating the release over time of a beneficial agent from devices made in accordance with this invention.

The devices were placed in test tubes containing phosphate buffered saline, maintained at 38° C. The amount of lysozyme released from each device was measured each day by ultraviolet spectroscopy. The average amount of lysozyme released from the devices was calculated and then plotted on a graph (FIG. 3). (The standard deviation is indicated by the bar through each point on the graph.)

The devices exhibited a mild, short, initial burst effect, subsequently releasing at a substantially constant rate. When the studies were terminated after 35 days, the devices were releasing an average of 1.7 mg/day and 62.6% of the lysozyme had been released (FIG. 4).

What is claimed is:

1. A partially coated device for the continuous administration of a beneficial agent in the body of a living being at a substantially steady rate which comprises:
   (a) a body fluid-contacting layer which comprises a dispersion of an agent which is substantially soluble in body fluid and a solid matrix material, said matrix material comprising a polymer which is substantially insoluble in said body fluid, and
   (b) a non-body fluid-contacting layer which comprises a reservoir of said beneficial agent, wherein said body fluid-contacting layer is compression molded to said non-body fluid-contacting layer to form a tablet or pellet.

2. A device in accordance with claim 1, which comprises more than one body fluid-contacting layer, wherein each of said body fluid contacting layers is compression molded to said non-body fluid-contacting layer.

3. The device of claim 1 or 2 wherein said matrix material is a comminuted polymer which is biocompatible with body tissue and body fluids.

4. The device of claim 3 wherein said polymer is selected from the group consisting of acyl substituted cellulose acetates and alkyl derivatives thereof, partially and completely hydrolyzed alkylene-vinyl acetate copolymers unplasticized polyvinyl chloride, cross-linked homo- and copolymers of polyvinyl acetate, cross-linked polyesters of acrylic and methacrylate, polyvinyl alkyl ethers, polyvinyl fluoride, silicone, polycarbonate, polyurethane, polyamide, polysulphones, styrene acrylonitrile copolymers, cross-linked poly(ethylene oxide) poly(alkylenes) poly(vinyl imidazole), poly(esters) and chlorosulphonated polyolefins.

5. The device of claim 4, wherein said polymer is an alkylene-vinyl acetate copolymer selected from the group consisting of ethylene vinyl acetate, ethylene vinyl methylacetate, ethylene-vinyl ethyl-acetate and ethylene-vinyl propylacetate.

6. The device of claim 1 or 2, wherein said beneficial agent comprises a drug, vitamin, nutritional supplement or biologically active protein.

7. The device of claim 6, wherein said beneficial agent is a drug selected from the group consisting of hypnotics, sedatives, tranquilizers, anti-convulsants, muscle relaxants, analgesics, anti-inflammatory agents, local anesthetics, antimicrobials, steroids, sympathomimetrics and diuretics.

8. The device of claim 6, wherein said agent is a biologically active protein.

9. The device of claim 1 or 2, wherein said non-body fluid-contacting layer additionally comprises a binder material.

10. The device of claim 9, wherein said non-body fluid contacting layer comprises a maximum of about 20 parts by weight binder to about 80 parts by weight beneficial agent.

11. The device of claim 10, wherein said non-body fluid contacting layer comprises about 10 parts by weight binder and about 90 parts by weight beneficial agent.

12. The device of claim 9 wherein said binder is selected from the group consisting of sodium bentonite, ethyl cellulose, stearic acid, calcium stearate, adipic acid, fumaric acid, polyethylene glycol and cellulose acetate.

13. The device of claim 9, wherein said binder comprises a polymeric material.

14. The device of claim 1 or 2, wherein said substantially body fluid-soluble agent is selected from the group consisting of sodium chloride, insulin and other water-soluble carbohydrates, lactose and other reducing sugars and sucrose and other non-reducing sugars.

15. The device of claim 14, wherein said agent is lactose.

16. The device of claim 14, wherein said agent is sucrose.

17. The device of claim 1 or 2, wherein said body fluid-contacting layer comprises a dispersion of beneficial agent and a solid polymeric matrix material.

18. The device of claim 1 or 2, wherein said body fluid-contacting layer comprises about 30 to about 70 parts by weight of said substantially body fluid-soluble agent and about 70 to about 30 parts by weight polymer.

19. The device of claim 18, wherein said body fluid-contacting layer comprises about 40 to about 60 parts by weight agent and about 60 to about 40 parts by weight polymer.

20. The device of claim 1 or 2, wherein after said layers have been compression molded into a tablet, said tablet is partially coated with a material substantially impermeable to said beneficial agent and said body fluid and substantially insoluble in said body fluid such that said non-body fluid-contacting layer of said tablet is coated.

21. The device of claim 1 or 2, wherein after said layers have been compression molded, the non-body fluid-contacting layer of said device is covered with a material essentially impermeable to said beneficial agent and said body fluid and essentially insoluble in said body fluid.

22. A method for the continuous administration of a beneficial agent to a living being at a substantially constant rate for a prolonged period time which comprises implanting the device of claim 1 or 2 into tissues of said living being.

23. A method for the continuous of a beneficial agent to a living being a substantially constant rate for a prolonged period of time which comprises inserting the device of claim 1 or 2 into a body cavity in the living being.

24. A method for the continuous administration of a beneficial agent to a living being at a substantially constant rate for a prolonged period of time which comprises the oral ingestion of the device of claim 1 or 2 by said living being.

* * * * *

UNITED STATES PATENT AND TRADEMARK OFFICE
CERTIFICATE OF CORRECTION

PATENT NO. : 4,898,733
DATED : February 6, 1990
INVENTOR(S) : Randolph B. DePrince and Ravi Viswanathan It is certified that error appears in the above-identified patent and that said Letters Patent is hereby corrected as shown below:

Column 9, line 3, Claim 22, following "period" insert --of--

Column 9, line 6, Claim 23, following "continuous" insert --administration--

Column 9, line 7, Claim 23, following "being" insert --at--

Signed and Sealed this

Fourth Day of December, 1990

Attest:

HARRY F. MANBECK, JR.

*Attesting Officer*  *Commissioner of Patents and Trademarks*